United States Patent
Kizaki et al.

(10) Patent No.: US 6,472,544 B1
(45) Date of Patent: Oct. 29, 2002

(54) PROCESS FOR THE PREPARATION OF OPTICALLY ACTIVE 2-[6-HYDROXYMETHYL)-1,3-DIOXAN-4YL] ACETIC ACID DERIVATIVES

(75) Inventors: Noriyuki Kizaki, Takasago; Yukio Yamada, Kakogawa; Yoshihiko Yasohara, Himeji; Akira Nishiyama, Kakogawa; Makoto Miyazaki, Osaka; Masaru Mitsuda, Akashi; Takeshi Kondo, Takasago; Noboru Ueyama, Kobe; Kenji Inoue, Kakogawa, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/509,998

(22) PCT Filed: Aug. 5, 1999

(86) PCT No.: PCT/JP99/04229

§ 371 (c)(1),
(2), (4) Date: Aug. 16, 2000

(87) PCT Pub. No.: WO00/08011

PCT Pub. Date: Feb. 17, 2000

(30) Foreign Application Priority Data

Aug. 5, 1998 (JP) .......................................... 10/221495
Jun. 4, 1999 (JP) .......................................... 11/158033

(51) Int. Cl.$^7$ .......................................... C07D 319/06
(52) U.S. Cl. ........................................ 549/333; 549/375
(58) Field of Search .................................. 549/333, 375

(56) References Cited

U.S. PATENT DOCUMENTS 4,970,313 A    11/1990   Wess et al.
5,155,251 A    10/1992   Butler et al.
5,278,313 A     1/1994   Thottathil et al.

FOREIGN PATENT DOCUMENTS

JP       05308977       11/1993
WO       WO 97/00968     1/1997

*Primary Examiner*—T. A. Solola
(74) *Attorney, Agent, or Firm*—Connolly Bove Lodge & Hutz LLP

(57) ABSTRACT

This invention provides a process for producing optically active 2-[6-(hydroxymethyl)-1,3-dioxan-4-yl]acetic acid derivatives, which are of value as intermediates of drugs, from inexpensive starting materials without using any special equipment such as that required for super-low temperature reactions.

A process for producing optically active 2-[6-(hydroxymethyl)-1,3-dioxan-4-yl]acetic acid derivatives which comprises reacting an acetic acid derivative at a temperature of not less than −30° C. with an enolate prepared by permitting either a base or a metal having a valency of 0 to act on the derivative to produce a hydroxyoxohexanoic acid derivative, reducing this compound with the aid of a strain of microorganism to provide a halomethyldioxanylacetic acid derivative, treating this compound with an acetalizing agent in the presence of an acid catalyst to provide a halomethyldioxanylacetic acid derivative, reacted with an acyloxylating agent to provide a acyloxymethyldioxanylacetic acid derivative, and subjecting this compound to solvolysis in the presence of a base.

22 Claims, No Drawings

PROCESS FOR THE PREPARATION OF OPTICALLY ACTIVE 2-[6-HYDROXYMETHYL)-1,3-DIOXAN-4YL] ACETIC ACID DERIVATIVES

This Appln. is a 371 of PCT/JP99/04229 filed Aug. 5, 1999.

TECHNICAL FIELD

The present invention relates to a process for producing optically active 2-[6-(hydroxymethyl)-1, 3-dioxan-4-yl]acetic acid derivatives which are of value as intermediates of drugs, particularly intermediates of HMG-CoA reductase inhibitors.

BACKGROUND ART

For the production of a 2-[6-(hydroxymethyl)-1,3-dioxan-4-yl]acetic acid derivative, the following processes are known.

(1) A process starting with 3-hydroxy-γ-butyrolactone to synthesize a 3,5,6-trihydroxyhexanoic acid ester derivative via a 3,5-dihydroxyhexanoic acid ester derivative (Japanese Kokai Publication Hei-4-173767).

(2) A process starting with 3,4-dihydroxybutyronitrile acetonide to synthesize a 3,5,6-trihydroxyhexanoic acid ester derivative via a 3,5-dihydroxyhexanoic acid ester derivative (Japanese Kokai Publication Hei-2-262537).

(3) A process starting with a 4-chloroacetoacetic acid ester to synthesize a 3,5,6-trihydroxyhexanoic acid ester derivative via conversion to a benzyloxy derivative, reduction and chain extension (Japanese Kokai Publication Hei-6-65226).

(4) A process starting with a 4-chloro-3-hydroxybutyric acid ester to synthesize a 3,5,6-trihydroxyhexanoic acid ester derivative through chain extension, reduction, etc. (USP 5278313).

(5) A process starting with malic acid to synthesize a 3,5,6-trihydroxyhexanoic acid ester via a 2,4-dihydroxyadipic acid derivative (Japanese Kokai Publication Hei-4-69355).

However, those processes involve reactions at a super-low temperature in the neighborhood of −80° C. (1, 2, 4, 5) or a hydrogenation reaction at a high pressure of 100 kg/cm² (3), thus requiring the use of special reaction equipment. Moreover, the processes involve the use of costly reagents in some stage or other and, therefore, none of them is an efficient process for commercial-scale production.

The prior art process (4), for instance, comprises reacting a 4-chloro-3-hydroxybutyric acid ester with an enolate of tert-butyl acetate using costly lithium hexamethyl disylazide at a super-low temperature of −78° C. in the first step and performing a stereoselective reduction using costly diethyl-methoxyborane and sodium borohydride, again at a super-low temperature of −78° C., in the second step. This process further involves an acetoxylation reaction with costly tetra-n-butylammonium acetate in the costly solvent 1-methyl-2-pyrrolidinone.

SUMMARY OF THE INVENTION

The present invention, developed in the above state of the art, has for its object to provide an expedient process for producing an optically active 2-[6-(hydroxymethyl)-1,3-dioxan-4-yl]acetic acid derivative of the following general formula (I) from inexpensive starting materials without using any special equipment such as that required for super-low temperature reactions.

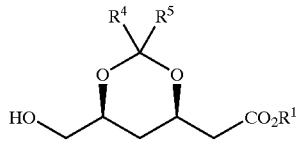

wherein $R_1$ represents hydrogen, an alkyl group of 1 to 12 carbon atoms, an aryl group of 6 to 12 carbon atoms or an aralkyl group of 7 to 12 carbon atoms, $R^4$ and $R^5$ each independently represents hydrogen, an alkyl group of 1 to 12 carbon atoms, an aryl group of 6 to 12 carbon atoms or an aralkyl group of 7 to 12 carbon atoms, and $R^4$ and $R^5$ may be conjoined each other to form a ring.

As the result of intensive investigations made in light of the above state of the art, the inventors of the present invention have developed an expedient process for producing an optically active 2-[6-(hydroxymethyl)-1,3-dioxan-4-yl]acetic acid derivative of the following general formula (I):

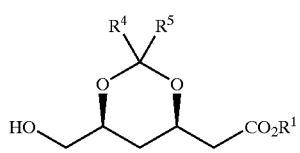

wherein $R^1$ represents hydrogen, an alkyl group of 1 to 12 carbon atoms, an aryl group of 6 to 12 carbon atoms or an aralkyl group of 7 to 12 carbon atoms, $R^4$ and $R^5$ each independently represents hydrogen, an alkyl group of 1 to 12 carbon atoms, an aryl group of 6 to 12 carbon atoms or an, aralkyl group of 7 to 12 carbon atoms, and $R^4$ and $R^5$ may be conjoined each other to form a ring, from inexpensive, readily available starting materials without employing any extraordinary equipment such as that required for low-temperature reactions.

The present invention, thus, is concerned with a process for producing said optically active 2-[6-(hydroxymethyl)-1, 3-dioxan-4-yl]acetic acid derivative (I):

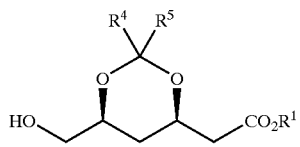

wherein $R^1$, $R^4$ and $R^5$ are respectively as defined below, which comprises (1) a step comprising reacting an enolate prepared by permitting either a base or a metal having a valency of 0 to act on an acetic ester derivative of the following general formula (II):

$$X^2CH_2CO_2R^1$$

wherein $R^1$ represents hydrogen, an alkyl group of 1 to 12 carbon atoms, an aryl group of 6 to 12 carbon atoms or an aralkyl group of 7 to 12 carbon atoms, $X^2$ represents hydrogen or a halogen atom, with a compound of the following general formula (III):

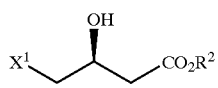

(III)

wherein $R^2$ represents an alkyl group of 1 to 12 carbon atoms, an aryl group of 6 to 12 carbon atoms or an aralkyl group of 7 to 12 carbon atoms, $X^1$ represents a halogen atom at a temperature of not less than −30° C. to give a compound of the following general formula (IV):

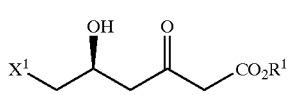

(IV)

wherein $R^1$ and $X^1$ are respectively as defined above,
(2) a step comprising reducing this compound with the aid of a strain of microorganism to give a compound of the following general formula (V):

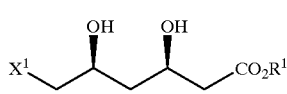

(V)

wherein $R^1$ and $X^1$ are respectively as defined above,
(3) a step comprising treating this compound with an acetalizing agent in the presence of an acid catalyst to give a compound of the following general formula (VI):

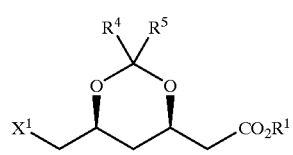

(VI)

wherein $R^1$ and $X^1$ are respectively as defined above, $R^4$ and $R^5$ each independently represents hydrogen, an alkyl group of 1 to 12 carbon atoms, an aryl group of 6 to 12 carbon atoms or an aralkyl group of 7 to 12 carbon atoms, and $R^4$ and $R^5$ may be conjoined each other to form a ring,
(4) a step comprising acyloxylating this compound with an acyloxylating agent to give a compound of the following general formula (VII):

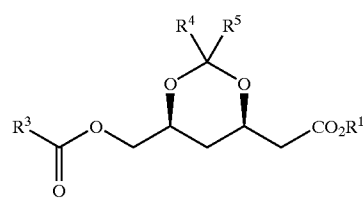

(VII)

wherein $R^1$, $R^4$ and $R^5$ are respectively as defined above, $R^3$ represents hydrogen, an alkyl group of 1 to 12 carbon atoms, an aryl group of 6 to 12 carbon atoms or an aralkyl group of 7 to 12 carbon atoms, and (5) a step comprising subjecting this compound to solvolysis in the presence of a base.

DISCLOSURE OF THE INVENTION

The present invention is now described in detail.

The present invention is constituted by 5 non-super-low-temperature reaction steps (1) to (5) as illustrated in the following reaction scheme.

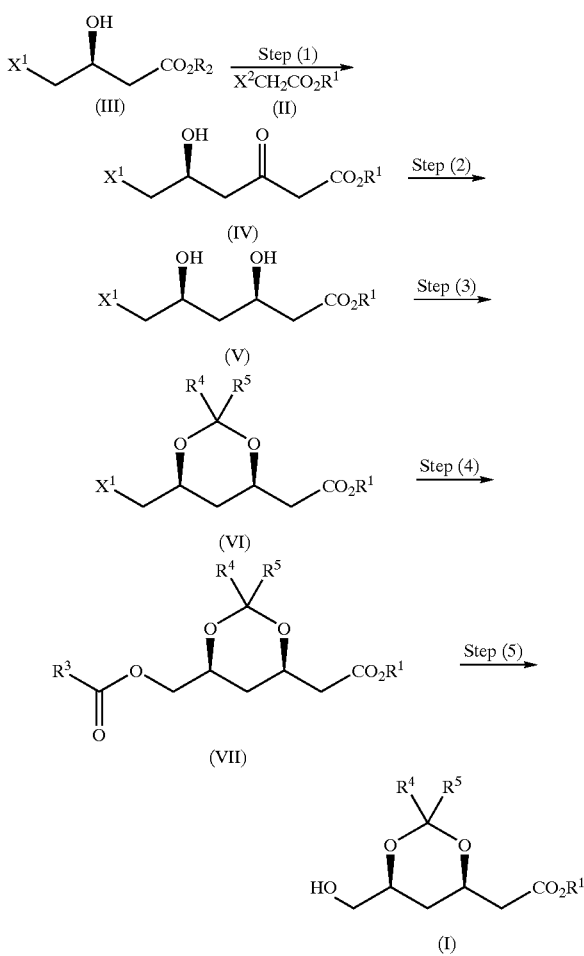

The following is a step-by-step description of the present invention. Step (1)

In this step, an enolate prepared by permitting either a base or a metal having a valency of 0 to act upon an acetic ester derivative of the following general formula (II):

(II)

is reacted with a (3S) configured hydroxybutyric acid ester derivative of the following general formula (III):

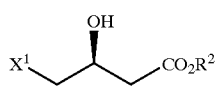

at a temperature of not less than −30° C. to produce a (5S)-configured hydroxyoxohexanoic acid derivative of the following general formula (IV):

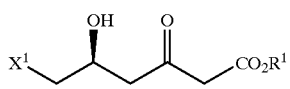

Generally when a reaction involving the enolate of an acetic ester or the like is conducted under non-super-low-temperature condition, e.g. at not less than −30° C., the self-condensation of the enolate proceeds predominantly to considerably detract from the conversion rate of the objective reaction. However, by the following procedure developed by the present inventors, the self-condensation of the acetic ester enolate can be minimized so that the objective reaction can be conducted with good yield.

In the hydroxybutyric acid derivative to be used in step (1), namely a compound of the following general formula (III):

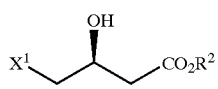

the configuration of the 3-position is (S) and $R^2$ is, for example, an alkyl group of 1 to 12 carbon atoms, an aryl group of 6 to 12 carbon atoms or an aralkyl group of 7 to 12 carbon atoms, thus as a specific example, there can be mentioned methyl, ethyl, i-propyl, tert-butyl, n-octyl, phenyl, naphthyl, p-methoxyphenyl and p-nitrobenzyl, among others. The preferred is methyl or ethyl, with ethyl being the more preferred.

$X^1$ represents a halogen atom, e.g. chloro, bromo and iodo, and is preferably chloro or bromo. The more preferred is chloro.

Optically active hydroxybutyric acid derivatives having the (3S) configuration can be produced on a high production scale by the known technology (inter alia, Japanese Patent Publication No.1723728).

Referring to the acetic ester derivative for use in step (1), $R^1$ represents hydrogen, an alkyl group of 1 to 12 carbon atoms, an aryl group of 6 to 12 carbon atoms or an aralkyl group of 7 to 12 carbon atoms, as a specific example, there can be mentioned hydrogen, methyl, ethyl, i-propyl, tert-butyl, n-octyl, phenyl, naphthyl, p-methoxyphenyl and p-nitrobenzyl, among others. The preferred is tert-butyl.

$X^2$ represents hydrogen or halogen, as a specific example, there can be mentioned hydrogen, chloro, bromo and iodo. The preferred species are hydrogen and bromo.

The amount of use of the acetic ester derivative is 1 to 10 molar equivalents, preferably 1 to 5 molar equivalents, relative to the hydroxybutyric acid.

In step (1), an enolate is first prepared by permitting either a base or a metal having a valency of 0 to act upon the acetic ester derivative.

Generally, a base is used in the preparation of its enolate when $X^2$ of the acetic ester is hydrogen, while a metal having a valency of 0 is used when $X^2$ is a halogen atom.

As the base which can be used in the preparation of the enolate, there can be mentioned lithium amide compounds such as lithium amide, lithium diisopropylamide, lithium dicyclohexylamide, lithium hexamethyl disylazide, etc.; magnesium amides such as magnesium chloride diisopropylamide, magnesium bromide diisopropylamide, magnesium iodide diisopropylamide, magnesium chloride dicyclohexylamide, etc.; sodium amides such as sodium amide, sodium diisopropylamide, etc., potassium amides such as potassium amide, potassium diisopropylamide, etc.; alkyllithium compounds such as methyllithium, n-butyllithium, t-butyllithium, etc.; Grignard reagents such as methylmagnesium bromide, i-propylmagnesium chloride, t-butylmagnesium chloride, etc.; metal alkoxides such as sodium methoxide, magnesium ethoxide, potassium tert-buthoxide, etc.; and metal hydrides such as lithium hydride, sodium hydride, potassium hydride, calcium hydride, etc.; among others.

The base is preferably a metal hydride, a magnesium amide, a lithium amide, or a Grignard reagent.

Those bases are used each alone or in combination. For example, a lithium amide or a metal hydride is more effective when used in combination with a Grignard reagent or a magnesium-containing base such as a magnesium amide.

The magnesium-containing base can be used in the combination of the base with a magnesium compound such as magnesium chloride, magnesium bromide or the like.

The magnesium amide can be represented by the following general formula (VIII):

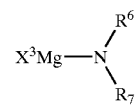

In the above formula, $R^6$ and $R^7$ each independently represents an alkyl group of 1 to 12 carbon atoms, an aryl group of 6 to 12 carbon atoms, an aralkyl group of 7 to 12 carbon atoms or a silyl group, as a specific example, there can be mentioned methyl, ethyl, i-propyl, tert-butyl, cyclohexyl, n-octyl, phenyl, naphthyl, p-methoxyphenyl, p-nitrobenzyl, trimethylsilyl, triethylsilyl, and phenyldimethylsilyl, among others. The preferred species is isopropyl. $X^3$ represents a halogen atom which is preferably chloro, bromo or iodo. The more preferred is chloro.

The magnesium amide can be prepared by the well-known method using a readily available secondary amide and a Grignard reagent (e.g. Japanese Kokai Publication Hei-8-523420). As an alternative, it can be prepared using a lithium amide and a magnesium halide in accordance with a known process (e.g. J. Org. Chem. 1991, 56, 5978-5980).

The lithium amide can be represented by the following general formula (X).

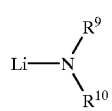

In the above formula, $R^9$ and $R^{10}$ each independently represents an alkyl group of 1 to 12 carbon atoms, an aryl group of 6 to 12 carbon atoms, an aralkyl group of 7 to 12 carbon atoms, or a silyl group, as a specific example, there can be mentioned methyl, ethyl, i-propyl, tert-butyl, cyclohexyl, n-octyl, phenyl, naphthyl, p-methoxyphenyl, p-nitrobenzyl, trimethylsilyl, triethylsilyl, and phenyldimethylsilyl. The preferred example is isopropyl.

The Grignard reagent is represented by the following general formula (IX):

In the formula, $R^8$ represents an alkyl group of 1 to 12 carbon atoms, an aryl group of 6 to 12 carbon atoms or an aralkyl group of 7 to 12 carbon atoms, as a specific example, there can be mentioned methyl, ethyl, n-propyl, i-propyl, n-butyl, tert-butyl, n-octyl, phenyl, naphthyl, p-methoxyphenyl and p-nitrobenzyl. The preferred is methyl, ethyl, i-propyl, n-butyl or tert-butyl. The still more preferred is tert-butyl. $X^4$ represents a halogen atom, which is preferably chloro, bromo or iodo. The more preferred is chloro.

The amount of use of the base in step (1) is 1 to 10 molar equivalents, preferably 2 to 6 molar equivalents, relative to the hydroxybutyric acid derivative.

The metal having a valency of 0 which can be used in the preparation of said enolate in step (1) includes zinc, magnesium, tin, etc. and is preferably zinc or magnesium.

The amount of use of the metal having a valency of 0 in step (1) is 1 to 20 molar equivalents, preferably 2 to 8 molar equivalents, relative to the hydroxybutyric acid derivative.

The solvent which can be used in step (1) may for example be an aprotic organic solvent. The organic solvent mentioned above includes hydrocarbon series solvents, such as benzene, toluene, n-hexane, cyclohexane, etc.; ether series solvents such as diethyl ether, tetrahydrofuran, 1,4-dioxane, methyl t-butyl ether, dimethoxyethane, ethylene glycol dimethyl ether, etc.; halogen-containing solvents such as methylene chloride, chloroform, 1,1,1-trichloroethane, etc.; and aprotic polar solvents such as dimethylformamide, N-methylpyrrolidone, hexamethylphorotriamide, etc., among others. These solvents can be used each alone or in a combination of two or more species. The preferred, among the above solvents, are hydrocarbon series solvents such as benzene, toluene, n-hexane, cyclohexane, etc. and ether series solvents such as diethyl ether, tetrahydrofuran, 1,4-dioxane, methyl t-butyl ether, dimethoxyethane, diethylene glycol dimethyl ether, etc. The more preferred are polyether series solvents such as dimethoxyethane and diethylene glycol dimethyl ether. Polyether series solvents may each be used as a sole solvent or an additive to a different reaction solvent. The addition amount in the latter case may be 1 to 10 molar equivalents relative to the hydroxybutyric acid derivative. The solvent which is particularly preferred is dimethoxyethane.

The reaction temperature for step (1) is preferably −30° C. to 100° C., more preferably −10° C. to 60° C.

In step (1), while the order of addition of reactants may be arbitrary, the hydroxybutyric acid derivative may be treated with the base beforehand. Preferably, it is treated with the base and the magnesium compound beforehand.

As the preferred base, there can be mentioned metal hydrides and lithium amides.

As the preferred magnesium compound, there can be mentioned magnesium chloride and magnesium bromide.

The base and the magnesium compound need not be independent compounds but a magnesium-containing base can be employed.

As the preferred magnesium-containing base, there can be mentioned Grignard reagents such as methylmagnesium bromide, i-propylmagnesium chloride, tert-butylmagnesium chloride, etc. and magnesium amides such as magnesium chloride diisopropylamide, magnesium bromide diisopropylamide, magnesium iodide diisopropylamide, magnesium chloride dicyclohexylamide and so forth.

At the pretreatment of the hydroxybutyric acid derivative, a pretreatment of a mixed solution of the hydroxybutyric acid derivative and acetic ester derivative is allowed. After this pretreatment, the reaction can be advantageously carried out by adding the base, such as a lithium amide, e.g. lithium amide, lithium diisopropylamide, lithium dicyclohexylamide or lithium hexamethyldisilazide, or a magnesium amide, or a solution of the base dropwise.

The proportion of the base for use in the pretreatment is 0.01 to 3 molar equivalents, preferably 0.5 to 1.5 molar equivalents, relative to the hydroxybutyric acid derivative.

The proportion of the magnesium compound for use in the pretreatment is 0.1 to 10 molar equivalents, preferably 0.5 to 1.5 molar equivalents, relative to the hydroxybutyric acid derivative.

The proportion of the magnesium-containing base for use in the pretreatment is 0.01 to 3 molar equivalents, preferably 0.5 to 1.5 molar equivalents, relative to the hydroxybutyric acid derivative.

The proportion of the base to be reacted after the pretreatment is 1 to 20 molar equivalents, preferably 2 to 8 molar equivalents, relative to the hydroxybutyric acid.

Thus, this step (1) can be advantageously carried out by treating the hydroxybutyric acid derivative with a base and a magnesium derivative in the first place and then causing a base to act on the same in the presence of an acetic ester derivative.

As an alternative, the hydroxybutyric acid derivative may be pretreated with a Grignard reagent and, then, reacted with an enolate prepared by permitting a metal having a valency of 0 to act on an acetic ester derivative.

After completion of the reaction in step (1), the reaction product can recovered from the reaction mixture by the routine after-treatment. For example, the reaction mixture after completion of reaction is mixed with the common inorganic or organic acid, e.g. hydrochloric acid, sulfuric acid, nitric acid, acetic acid or citric acid, and the mixture is then extracted with the common extraction solvent, e.g. ethyl acetate, diethyl ether, methylene chloride, toluene or hexane. From the extract obtained, the reaction solvent and extraction solvent are distilled off by heating under reduced pressure etc. isolate the objective compound. The product thus obtained is a substantially pure compound but may be further purified by a conventional technique such as recrystallization, fractional distillation, column chromatography or the like. Step (2)

In this step, the hydroxyoxohexanoic acid derivative obtained in step (1), namely a (5S)-configured hydroxyoxohexanoic derivative of the following general formula (IV);

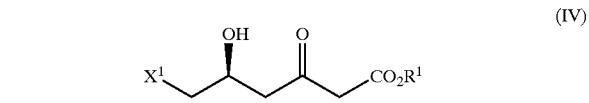

is subjected to the reduction with a strain of microorganism to provide a (3R,5S)-configured dihydroxyhexanoic acid derivative of the following general formula (V).

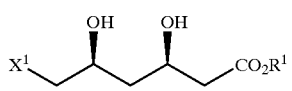

(V)

In the case of the stereoselective reduction of the carbonyl group of such a hydroxyoxohexanoic acid derivative, the technique is generally adapted in which the reduction reaction is carried out with a hydride series reducing agent such as sodium borohydride in the presence of an alkylborane at a super-low temperature (e.g. U.S. Pat. No. 5278313).

The inventors of the present invention developed a microbiological reduction technology by which a hydroxyoxohexanoic acid derivative can be reduced at low cost with good stereoselectivity at a non-super-low temperature.

The microorganism capable of reducing a hydroxyoxohexanoic acid derivative to a dihydroxyhexanoic acid derivative, which is for use in this step (2), can be selected by the method described below. For example, a 500-mL Sakaguchi flask is charged with 50 mL of Medium A (pH 6.5) comprising 5% of glucose, 0.5% of peptone, 0.2% of potassium dihydrogen phosphate, 0.1% of dipotassium hydrogen phosphate, 0.02% of magnesium sulfate and 0.1% of yeast extract. After sterilization, the flask is inoculated with a strain of microorganism and incubated under shaking at 30° C. for 2 to 3 days. The cells are harvested by centrifugation and suspended in 25 mL of a phosphate buffer solution containing 0.1 to 0.5% of tert-butyl (5S)-6-chloro-5-hydroxy-3-oxohexanoate and 5% of glucose, and the resulting suspension is shaken in a 500-mL Sakaguchi flask at 30° C. for 2 to 3 days. After completion of the conversion reaction, the reaction mixture is extracted with one volume of ethyl acetate and the extract is analyzed for tert-butyl 6-chloro-3,5-dihydroxyhexanoate by high performance liquid chromatography [column: Nakalai Tesque's Cosmocil 5CN-R (4.6 mm×250 mm), eluent: 1 mM phosphoric acid/water:acetonitrile=5:1, flow rate: 0.7 mL/min., detection at 210 nm, column temperature 30° C., elution time [tert-butyl (3S,5S)-6-chloro-3,5-dihydroxyhexanoate: 12.5 min.; terty-butyl (3R,5S)-6-chloro-3,5-dihydroxyhexanoate: 13.5 min., tert-butyl (5S)-6-chloro-5-hydroxy-3-oxohexanoate: 17 min.].

The bacterial strain capable of reducing a hydroxyoxohexanoic acid derivative to a dihydroxyhexanoic acid derivative, which can be used in step (2), can be selected by the method described below. For example, a large-sized test tube is charged with 7 mL of Medium B (pH 7.0) comprising 1% of meat extract, 1% of polypeptone, 0.5% of yeast extract and 0.5% of glucose. After sterilization, the test tube is inoculated with a test strain and shake culture is carried out at 30° C. for ½ day. The cells are harvested by centrifugation and suspended in 0.5 mL of a phosphate buffer solution containing 0.1 to 0.5% of tert-butyl (5S)-6-chloro-5-hydroxy-3-oxohexanoate and glucose. This suspension is shaken in a 10-mL stoppered test tube at 30° C. for 1~2 days. After completion of the conversion reaction, the reaction mixture is extracted by adding one volume of ethyl acetate and the extract is analyzed for tert-butyl 6-chloro-3,5-dihydroxyhexanoate by high performance liquid chromatography.

As the strains of microorganism which can be used in the practice of this invention, there can be mentioned those belonging to the genera Hormoascus, Candida, Cryptococcus, Debaryomyces, Geotrichum, Kuraishia, Hansenulla, Kluyveromyces, Pichia, Yamadazyma, Rhodotorula, Saccharomyces, Schizoblastosporon, and Zygosaccharomyces. More particularly, there can be used such strains as *Hormoascus platypodis* IFO1471, *Candida catenulata* IFO0745, *Candida diversa* IFO1019, *Candida fructus* IFO1581, *Candida glaebosa* IFO1353, *Candida guilliermondii* IFO0454, *Cryptococcus humicola* IFO0760, *Candida intermedia* IFO0761, *Candida magnoliae* IFO0705, *Candida musae* IFO1582, *Candida pintolopesii* var. *pintolopenii* IFO0729, *Candida pinus* IFO0741, *Candida sake* IFO0435, *Candida sonorensis* IFO10027, *Candida tropicalis* IFO1401, *Cryptococcus laurentii* IFO0609, *Cryptococcus terreus* IFO0727, *Debaryomyces hansenii* var. *fabryi* IFO0058, *Geotrichum eriense* ATCC22311, *Kuraishia capsulata* IFO0721, *Kluyveromyces marxianus* IFO00288, *Pichia bovis* IFO1886, *Yamadazyma haplophila* IFO0947, *Pichia membranaefaciens* IFO0458, *Rhodotorula glutinis* IFO1099, *Saccharomyces cerevisiae* IFO0718, *Schizoblastosporon kobayasii* IFO1644, *Candida claussenii* IFO0759, *Debaryomyces robertsii* IFO1277 and *Zygosaccharomyces rouxii* IFO0493, among others. Those microorganisms can be generally obtained, free of cost or at cost, from culture collections which are readily accessible. Or they may be isolated from the natural kingdom. Furthermore, those microorganisms may be subjected to mutation to derive strains having the more favorable characters for the present reaction.

While the microorganisms which can be used in the present invention include bacteria of the genera Brevibacterium, Corynebacterium, and Rhodococcus, specifically the following bacterial strains, among others, can be used. *Brevibacterium stationis* IFO12144, *Corynebacterium ammoniagenes* IFO12072, *Corynebacterium flavescens* IFO14136, *Corynebacterium glutamicum* ATCC13287, *Rhodococcus erythropolis* IAM1474. Those microorganisms can be generally obtained, free of cost or at cost, from culture collections which are readily accessible. Or they may be isolated from the natural kingdom. Furthermore, these bacteria may be subjected to mutation to derive strains having the more favorable characters for the present reaction.

In cultivation of the above-mentioned strains of microorganisms, any nutrient source is utilized by microorganisms in general. For example, as sources of carbon, there can be used various sugars such as glucose, sucrose, maltose, etc.; organic acids such as lactic acid, acetic acid, citric acid, propionic acid, etc.; alcohols such as ethanol, glycerol, etc.; hydrocarbons such as paraffin etc.; oils such as soybean oil, rapeseed oil, etc.; and various mixtures thereof. As sources of nitrogen there can be used a variety of nitrogenous substances such as ammonium sulfate, ammonium phosphate, urea, yeast extract, meat extract, peptone, and corn steep liquor, among others. The culture medium may be further supplemented with inorganic salts, vitamins and other nutrients.

Culture of microorganisms can be generally carried out under routine conditions, for example within the range of pH 4.0 to 9.5 at a temperature 20 to 45° C. aerobically for 10 to 96 hours. In permitting a strain of microorganism to act on the hydroxyoxohexanoic acid derivative, generally the culture broth obtained can be submitted as it is to the reaction but a concentrate of the broth can also be employed. Moreover, in case some component in the culture broth is suspected to adversely affect the reaction, the cells separated by, for example, centrifugation of the broth can be used as such or after further processing.

The product available after said further processing is not particularly restricted but there can be mentioned dried cells which can be obtained by dehydration with acetone or diphosphorous pentoxide or drying over a desiccant or with the draft air of a fan, the product of surfactant treatment, the product of bacteriolytic enzyme treatment, immobilized cells, and a cell-free extract obtainable from disrupted cells. A still further alternative comprises purifying the enzyme catalyzing a chiral reduction reaction from the culture broth and employ the purified enzyme.

In conducting the reduction reaction, the substrate hydroxyoxohexanoic acid derivative may be added en bloc at initiation of the reaction or in several installments as the reaction proceeds.

The reaction temperature is generally 10 to 60° C., preferably 20 to 40° C., and the reaction pH is 2.5 to 9, preferably 5 to 9.

The concentration of the microbes in the reaction system can be judiciously selected according to the ability of the strain to reduce the substrate. The substrate concentration of the reaction system is preferably 0.01 to 50% (w/v), more preferably 0.1 to 30%.

The reaction is generally carried out under shaking or under aeration and stirring. The reaction time setting is selected according to the substrate concentration, the concentration of the microbes, and other reaction conditions. It is generally preferable to set various conditions so that the reaction will go to completion in 2 to 168 hours.

For the purpose of accelerating the reduction reaction, an energy source, such as glucose or ethanol, can be added at the amount of 1 to 30% to the reaction mixture with advantage. Moreover, the reaction can be accelerated by adding a coenzyme, such as reduced nicotinamide adenine dinucleotide (NADH) or reduced nicotinamide adenine dinucleotide phosphate (NADPH), which is known to be generally necessary for biological reduction systems in general. Thus, such a coenzyme may be directly added to the reaction mixture or, alternatively, a reaction system giving rise to NADH or NADPH and an oxidized-form coenzyme may be added together to the reaction mixture. For example, a reaction system in which formate dehydrogenase reduces NAD to NADH when carbon dioxide and water are produced from formic acid or a reaction system in which glucose dehydrogenase reduces NAD or NADP to NADH or NADPH when gluconolactone is produced from glucose can be utilized. It is also useful to add a surfactant such as Triton (Nakalai-Tesque), Span (Kanto Chemical) or Tween (Nakalal-Tesque) to the reaction system. Furthermore, for the purpose of obviating the inhibition of the reaction by the substrate and/or the reduction product alcohol, a water-insoluble organic solvent such as ethyl acetate, butyl acetate, isopropyl ether, toluene or the like can be added to the reaction system. Moreover, for enhancing the solubility of the substrate, a water-soluble organic solvent such as methanol, ethanol, acetone, tetrahydrofuran or dimethyl sulfoxide can be added.

The reduction product dihydroxyhexanoic acid derivative can be harvested directly from the culture broth or isolated from harvested cells by extraction with a solvent such as ethyl acetate, toluene or the like, followed by removal of the solvent. The product may be further purified by recrystallization, silica gel column chromatography or the like procedure to provide the dihydroxyhexanoic acid derivative of higher purity. Step (3)

In this step, the (3R,5S)-configured dihydroxyhexanoic acid derivative obtained in step (2), namely the compound of the following general formula (V):

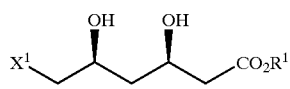

(V)

is subjected to the known acetalization reaction, for example treatment with an acetalizing agent in the presence of an acid catalyst, to provide a (4R,6S)-configured halomethyldioxanylacetic acid derivative of the following general formula (VI).

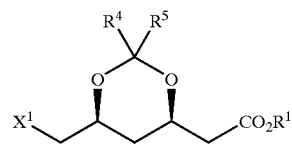

(VI)

As the acetalizing agent which can be used in this step (3), there can be mentioned ketones, aldehydes, alkoxyalkanes, and alkoxyalkenes. As specific examples of said ketones, aldehydes, alkoxyalkanes and alkoxyalkenes, there can be mentioned acetone, cyclohexanone, formaldehyde, benzaldehyde, dimethoxymethane, 2,2-dimethoxypropane, 2-methoxypropene, 1,1-dimethoxycyclohexane, and so forth. The preferred acetalizing agents are acetone, 2-methoxypropene and 2,2-dimethoxypropane.

The amount of the acetalizing agent to be used in step (3) is preferably 1 to 10 molar equivalents, more preferably 1 to 5 molar equivalents, relative to the dihydroxyhexanoic acid derivative. For expediting the reaction, the acetalizing agent can be utilized as the reaction solvent.

The acid catalyst which can be used in step (3) is a Lewis acid or a Brønstead acid. As the Lewis acid and Brønstead acid mentioned above, there can be mentioned such Lewis acids as aluminum trichloride, boron trifluoride, zinc dichloride, tin tetrachloride, etc.; carboxylic acids such as oxalic acid, formic acid, acetic acid, benzoic acid, trifluoroacetic acid, etc.; sulfonic acids such as methanesulfonic acid, p-toluenesulfonic acid, camphorsulfonic acid, pyridinium p-toluenesulfonate, etc.; and inorganic acids such as hydrochloric acid, sulfuric acid, nitric acid and boric acid. The preferred are p-toluenesulfonic acid, camphorsulfonic acid and pyridinium p-toluenesulfonate.

The amount of the acid catalyst to be used in step (3) is preferably 0.001 to 0.5 molar equivalent, more preferably 0.005 to 0.1 molar equivalent, relative to the dihydroxyhexanoic acid derivative.

The reaction in step (3) can be carried out in the absence of a solvent but various organic solvents can be used as a reaction solvent. As such organic solvents, there can be mentioned hydrocarbon series solvents such as benzene, toluene, cyclohexane, etc.; ether series solvents such as diethyl ether, tetrahydrofuran, 1,4-dioxane, methyl t-butyl ether, dimethoxyethane, etc.; ester series solvents such as ethyl acetate, butyl acetate, etc.; ketone series solvents such as acetone, methyl ethyl ketone, etc.; halogen-containing solvents such as methylene chloride, chloroform, 1,1,1-trichloroethane, etc.; nitrogen-containing solvents such as dimethylformamide, acetamide, formamide, acetonitrile, etc.; and aprotic polar solvents such as dimethyl sulfoxide, N-methylpyrrolidone, hexamethylphosphoric triamide, etc., among others. These organic solvents can be used each alone or in a combination of two or more species. The preferred solvents are toluene, acetone, methylene chloride, tetrahydrofuran, dimethylformamide, acetamide, formamide, acetonitrile, dimethyl sulfoxide and N-methylpyrrolidone.

The reaction temperature in step (3) is −20° C. to 100° C., preferably 0 to 50° C.

After completion of the reaction in step (3), the product can be recovered from the reaction mixture by the routine after-treatment. A typical after-treatment comprises adding water to the reaction mixture upon completion of the reaction, carrying out an extraction using the common extraction solvent, such as ethyl acetate, diethyl ether, methylene chloride, toluene or hexane, and removing the reaction solvent and extraction solvent from the extract by, for example, distillation by heating under reduced pressure to provide the objective product. An alternative after-treatment comprises distilling off the reaction solvent by heating under reduced pressure immediately following the reaction and, then, carrying out the same procedure as above. The objective product thus obtained is substantially pure but may be further purified by the conventional procedure such as recrystallization, fractional distillation or chromatography.

In the compound thus obtained in step (3), i.e. a halomethyldioxanylacetic acid derivative of the following general formula (VI):

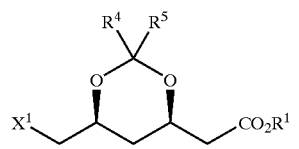

(VI)

wherein $R^4$ and $R^5$ may each independently be a hydrogen atom, an alkyl group of 1 to 12 carbon atoms, an aryl group of 6 to 12 carbon atoms or an aralkyl group of 7 to 12 carbon atoms, thus including methyl, ethyl, tert-butyl, hexyl, phenyl, benzyl and p-methoxybenzyl, among others. Of these, methyl is preferred.

$R^4$ and $R^5$ may be conjoined each other to form a ring, for example, $R^4$ and $R^5$ may form a cyclopentane ring, a cyclohexane ring, a cycloheptane ring or a benzocyclopentane ring therebetween to constitute a Spiro system with the 1,3-dioxane ring. Step (4)

In this step, the compound obtained in step (3), namely (4R,6S)-configured halomethyldioxanylacetic acid derivative of the following general formula (VI):

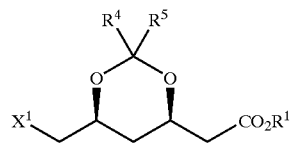

(VI)

is reacted with an acyloxylating agent to provide a (4R,6S)-configured acyloxymethyldioxanylacetic acid derivative of the following general formula (VII):

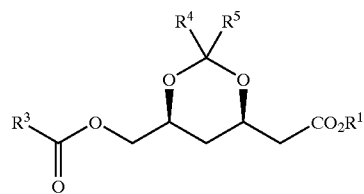

(VII)

In the above formula, $R^3$ may for example be a hydrogen atom, an alkyl group of 1 to 12 carbon atoms, an aryl group of 6 to 12 carbon atoms or an aralkyl group of 7 to 12 carbon atoms, thus specifically including hydrogen, methyl, ethyl, n-propyl, i-propyl, n-butyl, tert-butyl, n-octyl, phenyl, naphthyl, p-methoxyphenyl, and p-nitrobenzyl, among others. Of these groups, methyl is the most preferred.

As the acyloxylating agent for use in this step (4), there can be mentioned carboxylic acid quaternary ammonium salts of the following general formula (XI):

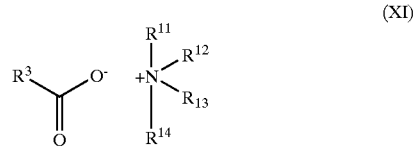

(XI)

Here, $R^{11}$, $R^{12}$, $R^{13}$ and $R^{14}$ each independently represents an alkyl group of 1 to 12 carbon atoms, an aryl group of 6 to 12 carbon atoms or an aralkyl group of 7 to 12 carbon atoms, thus including methyl, ethyl, n-propyl, i-propyl, n-butyl, tert-butyl, n-octyl, phenyl, naphthyl, p-methoxyphenyl and p-nitrobenzyl, among others. Among these, n-butyl is preferred.

The amount of use of the carboxylic acid quaternary ammonium salt is 1 to 5 molar equivalents, preferably 1 to 3 molar equivalents, relative to-the halomethyldioxanylacetic acid derivative.

Aside from said carboxylic acid quaternary ammonium salt, a mixture of a quaternary ammonium salt of the following general formula (XII);

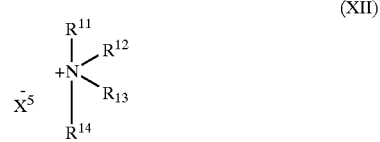

(XII)

and a carboxylic acid salt of the following general formula (XIII);

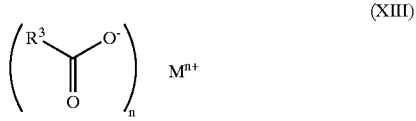

(XIII)

for instance, can be used likewise as the acyloxylating agent in step (4).

The acyloxylation reaction using the above mixture of a quaternary ammonium salt and a carboxylic acid salt represents a route of synthesis which does not require said expensive carboxylic acid quaternary ammonium salt but involves only the use of a less expensive quaternary ammonium salt in a smaller amount and is a novel reaction technology developed by the inventors of the present invention.

In the above quaternary ammonium salt, $R^{15}$, $R^{16}$, $R^{17}$ and $R^{18}$ may each independently be an alkyl group of 1 to 12 carbon atoms, an aryl group of 6 to 12 carbon atoms or an aralkyl group of 7 to 12 carbon atoms, thus including methyl, ethyl, n-propyl, i-propyl, n-butyl, tert-butyl, n-octyl, phenyl, naphthyl, p-methoxyphenyl and p-nitrobenzyl, among others. Preferred is n-butyl.

$X^5$ may for example be a halogen atom, a hydroxyl group or an acyloxy group. Specifically, chlorine, bromine, iodine, hydroxy, acetoxy, butyloxy, benzyloxy, trifluoroacetoxy, etc. can be mentioned and, among them, chlorine, bromine, hydroxy and acetoxy are preferred. Of these, chlorine or bromine is still more preferred.

The amount of use of said quaternary ammonium salt is 0.05 to 2 molar equivalents, preferably not more than a catalytic amount or specifically 0.1 to 0.9 molar equivalent, relative to the halomethyldioxanylacetic acid derivative.

In the above carboxylic acid salt, $R^3$ may for example be a hydrogen atom, an alkyl group of 1 to 12 carbon atoms, an aryl group of 6 to 12 carbon atoms or an aralkyl group of 7 to 12 carbon atoms, thus including hydrogen, methyl, ethyl, n-propyl, i-propyl, n-butyl, tert-butyl, n-octyl, phenyl, naphthyl, n-methoxyphenyl and p-nitrobenzyl, among others. Among these, methyl is preferred.

M represents an alkali metal or an alkaline earth metal, thus including lithium, sodium, potassium, magnesium, calcium and barium, among others. The preferred metals are sodium and potassium.

The symbol n represents an integer of 1 or 2 depending on the valence of M.

The amount of use of said carboxylic acid salt is 1 to 15 molar equivalents, preferably 1 to 5 molar equivalents, relative to the halomethyldioxanylacetic acid derivative.

The preferred combinations of $X^5$ in the quaternary ammonium salt with M in the carboxylic acid salt are the combination of chlorine for $X^5$ in said quaternary ammonium salt with sodium for M in said carboxylic acid salt and the combination of bromine for $X^5$ in said quaternary ammonium salt with potassium for M in said carboxylic acid salt.

For the reaction in step (4), various organic solvents can be used as the reaction solvent. As such organic solvents, there can be mentioned hydrocarbon series solvents such as benzene, toluene, cyclohexane, etc.; ether series solvents such as diethyl ether, tetrahydrofuran, 1,4-dioxane, methyl t-butyl ether, dimethoxyethane, etc.; ester series solvents such as ethyl acetate, butyl acetate, etc.; halogen-containing solvents such as methylene chloride, chloroform, 1,1,1-trichloroethane, etc.; nitrogen-containing solvents such as N,N-dimethylformamide, acetamide, formamide, acetonitrile, etc.; and aprotic polar solvents such as dimethyl sulfoxide, N-methylpyrrolidone, hexamethylphosphoric triamide, etc. Those organic solvents can be used each alone or in a combination of two or more species. The preferred solvents are nitrogen-containing solvents such as N,N-dimethylformamide, acetamide, formamide, acetonitrile, etc.; and aprotic polar solvents such as dimethyl sulfoxide, N-methylpyrrolidone, hexamethylphosphoric triamide, etc., with N,N-dimethylformamide being more preferred.

The reaction temperature in step (4) is 0° C. to 200° C., preferably 50 to 150° C.

After completion of the reaction in step (4), the product can be recovered from the reaction mixture by the routine after-treatment. A typical after-treatment comprises adding water to the reaction mixture upon completion of the reaction and carrying out an extraction using the common extraction solvent, such as ethyl acetate, diethyl ether, methylene chloride, toluene, hexane or heptane, and removing the reaction solvent and extraction solvent from the resulting extract by, for example, distillation by heating under reduced pressure to provide the objective product. An alternative method comprises distilling off the reaction solvent by heating under reduced pressure immediately after completion of the reaction and, then, carrying out the same procedure as above. The objective product thus obtained is substantially pure but may be further purified by the conventional procedure such as recrystallization, fractional distillation or chromatography. Step (5)

In this step, the compound obtained in step (4), namely a (4R,6S)-configured acyloxymethyldioxanylacetic acid derivative of the following general formula (VII):

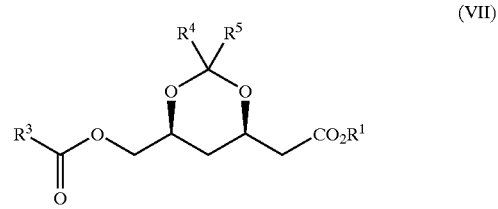

is subjected to solvolysis in the presence of a base according to a known method, for instance, to provide the corresponding (4R,6S)-configured hydroxymethyldioxanylacetic acid derivative of the following general formula (I):

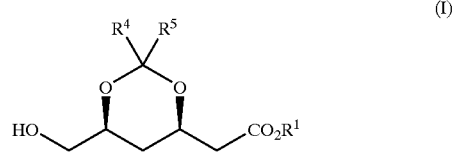

As the base which can be used for this solvolysis in step (5), there can be mentioned eboth inorganic and organic bases such as sodium carbonate, potassium carbonate, sodium hydrogencarbonate, potassium hydrogencarbonate, sodium hydroxide, potassium hydroxide, calcium hydroxide, lithium hydroxide, barium hydroxide, magnesium hydroxide, sodium acetate, potassium acetate, ammonia, triethylamine, pyridine, piperidine, N,N-dimethylaminopyridine and so forth. The preferred base is potassium carbonate.

The amount of use of the base in this reaction is 0.001 to 5 equivalents, preferably 0.01 to 1.0 equivalent, relative to the acyloxymethyldioxanylacetic acid derivative.

The solvolysis reaction in step (5) is carried out in water or a protic organic solvent, or a mixture of either water or a protic organic solvent with an aprotic organic solvent. As the protic organic solvent mentioned above, there can be mentioned alcohol series solvents such as methanol, ethanol, butanol, isopropyl alcohol, ethylene glycol, methoxyethanol, etc. and amine series solvents such as diethylamine, pyrrolidine, piperidine and so forth. As the aprotic organic solvent mentioned above, there can be mentioned hydrocarbon series solvents such as benzene, toluene, cyclohexane, etc.; ether series solvents such as diethyl ether, tetrahydrofuran, 1,4-dioxane, methyl t-butyl ether, dimethoxyethane, etc.; ester series solvents such as ethyl acetate, butyl acetate, etc.; ketone series solvents such as acetone, methyl ethyl ketone, etc.; halogen-containing solvents such as methylene chloride, chloroform, 1,1,1-trichloroethane, etc.; nitrogen-containing solvents such as dimethylformamide, acetonitrile, etc.; and aprotic polar solvents such as dimethyl sulfoxide, N-methylpyrrolidone, hexamethylphosphoric triamide and so forth.

The preferred reaction solvent includes water, methanol and ethanol.

The reaction temperature in step (5) is −20° C. to 100° C., preferably −10 to 50° C.

After completion of the reaction, the reaction product can be recovered from the reaction mixture by the routine after-treatment method. A typical after-treatment method comprises adding water to the reaction-mixture at the end of the reaction, extracting the reaction product into the common solvent such as ethyl acetate, diethyl ether, methylene chloride, toluene or hexane and removing the reaction solvent and extraction solvent by heating under reduced pressure to thereby isolate the objective. compound. An alternative method comprises removing the reaction solvent, for example by heating under reduced pressure, immediately after completion of the reaction and, then, carrying out the same procedure as above. The objective compound thus obtained is substantially pure but may be further purified by the routine procedure such as recrystallization, fractional distillation or chromatography.

BEST MODE FOR CARRYING OUT THE INVENTION

The following examples illustrate the present invention in further detail but are not intended to define the scope of the invention.

EXAMPLE 1

Tert-butyl(5S)-6-chloro-5-hydroxy-3-oxohexanoate

Under argon gas, 3.34 g (33 mmol) of diisopropylamine was added dropwise to 16.7 g (30 mmol) of n-butylmagnesium chloride in toluene/tetrahydrofuran (weight ratio=1:2.5) (1.8 mol/kg) at 40° C. with constant starring to prepare a magnesium chloride diisopropylamide solution.

Separately, 1.0 g (6.0 mmol) of ethyl(3S)-4-chloro-3-hydroxybutyrate (Japanese Patent Publication No.1723728) and 1.74 g (15 mmol) of tert-butyl acetate were dissolved in 5.0 mL of dimethoxyethane and the solution was stirred under argon gas at 0 to 5° C. To this solution was added the above magnesium chloride diisopropylamide solution dropwise over 3 hours, and the mixture was further stirred at 20° C. for 16 hours.

Using a separate vessel, 7.88 g of concentrated hydrochloric acid, 20 g of water and 20 mL of ethyl acetate were mixed together under stirring and the above reaction mixture was poured into this vessel. After standing, the organic layer was separated, washed with saturated aqueous sodium chloride solution and dried over anhydrous magnesium sulfate and the solvent was distilled off by heating under reduced pressure.

The residue was purified by silica gel column chromatography (Merck, Kieselgel 60, hexane:ethyl acetate=80:20) to provide 1.14 g of tert-butyl(5S)-6-chloro-5-hydroxy-3-oxohexanoate (colorless oil) in an yield of 80%. $^1$H-NMR (CDCl$_3$, 400 MHz/ppm): 1.48 (9H, s), 2.84 (1H, dd), 2.91 (1H, dd), 3.05 (1H, bs), 3.41 (2H, s), 3.55–3.64 (2H, m), 4.28–4.36 (1H, m)

Comparative Example 1

Tert-butyl(5S)-6-chloro-5-hydroxy-3-oxohexanoate

In 5.0 mL of tetrahydrofuran were dissolved 1.0 g (6.0 mmol) of ethyl(3S)-4-chloro-3-hydroxybutyrate and 2.78 g (24 mmol) of tert-butyl acetate, followed by stirring under argon gas at 0 to 5° C. To this solution was added a tetrahydrofuran solution containing 24 mmol of lithium diisopropylamide dropwise over 20 minutes, and the mixture was further stirred at 5 to 20° C. for 16 hours.

In a separate vessel, 6.31 g of concentrated hydrochloric acid, 20 g of water and 20 mL of ethyl acetate were mixed by stirring and the above reaction mixture was poured in the mixture. After standing, the organic layer was separated, washed with saturated sodium chloride/H$_2$0 and dehydrated over anhydrous magnesium sulfate and the solvent was then distilled off by heating under reduced pressure.

The residue was purified by silica gel column chromatography (Merck's Kieselgel 60, hexane:ethyl acetate= 80:20) to provide 86 mg (colorless oil) of tert-butyl(5S)-6-chloro-5-hydroxy-3-oxohexanoate in a yield of 6%.

EXAMPLE 2

Tert-butyl(5S)-6-chloro-5-hydroxy-3-oxohexanoate

In 10.0 mL of tetrahydrofuran were dissolved 3.0 g (18.0 mmol) of ethyl(3S)-4-chloro-3-hydroxybutyrate, 5.22 g (45 mmol) of tert-butyl acetate, and 6.86 g (72 mmol) of magnesium chloride, and the solution was stirred under argon gas at 0 to 5° C. To this solution was added a tetrahydrofuran solution containing 90 mmol lithium diisopropylamide dropwise over one hour, and the mixture was further stirred at 25° C. for 3 hours.

In a separate vessel, 21.7 g of concentrated hydrochloric acid, 30 g of water and 30 mL of ethyl acetate were mixed by stirring and the above reaction mixture was poured in this mixture. After standing, the organic layer was separated and washed with water twice and the solvent was then distilled off by heating under reduced pressure to provide 5.62 g of a red oil containing tert-butyl (5S)-6-chloro-5-hydroxy-3-oxohexanoate.

This oil was analyzed by high performance liquid chromatography (column: Nakalai-Tesque, Cosmoseal 5CN-R (4.6 mm×250 mm), eluent:water/acetonitrile=9/1, flow rate 1.0 mL/min, detection at 210 nm, column temperature 40° C.). The reaction yield thus found was 65%.

EXAMPLE 3

Tert-butyl(5S)-6-chloro-5-hydroxy-3-oxohexanoate

Under argon gas, a solution composed of 26.71 g (264 mmol) of diisopropylamine and 18.8 g of tetrahydrofuran was added dropwise to 150 mL (240 mmol) of a solution of n-butyllithium (1.6 mol/L) in hexane to prepare a lithium diisopropylamide solution.

In 20 mL of tetrahydrofuran were dissolved 12.5 g (75 mmol) of ethyl(3S)-4-chloro-3-hydroxybutyrate and 17.4 g (150 mmol) of tert-butyl acetate, and the resulting solution was stirred under argon gas at 0 to 5° C. To this solution was added 42.9 g (75 mmol) of a solution of tert-butylmagnesium chloride in toluene/tetrahydrofuran; (1:2.5 by weight) (1.8 mol/kg) dropwise over 30 minutes, and the whole mixture was further stirred at 5° C. for 30 minutes. Then, the lithium diisopropylamine solution prepared above was added dropwise over 3 hours, and the resulting mixture was further stirred at 5° C. for 16 hours.

In a separate vessel, 60.38 g of concentrated hydrochloric acid, 31.3 g of water and 50 mL of ethyl acetate were mixed by stirring, and the above reaction mixture was poured in this mixture. After standing, the organic layer was separated and washed twice with water and the solvent was distilled off by heating under reduced pressure to provide 22.0 g of a red oil containing tert-butyl (5S)-6-chloro-5-hydroxy-3-oxohexanoate.

As analyzed by the method described in Example 2, the reaction yield was 78%.

EXAMPLE 4

Tert-butyl(3R,5S)-6-chloro-3,5-dihydroxyhexanoate

Sakaguchi flasks of 500 mL capacity were respectively charged with 50 mL of said medium A and, after sterilization, inoculated with the microbial strains indicated in Table 1, respectively. Aerobic shake culture was then carried out at 30° C. for 2 days. From each of the culture broths, the cells were harvested by centrifugation and suspended in 25 mL of 50 mM phosphate buffer (pH 6.5) containing 1% of tert-butyl(5S)-6-chloro-5-hydroxy-3-oxohexanoate (synthesized by the process described in Example 1) and 2% of glucose. The suspension was put in a 500 mL Sakaguchi flask and a reaction was conducted under shaking at 30° C. for 20 hours. After completion of the reaction, the reaction mixture was extracted twice with one volume of ethyl acetate each and the ethyl acetate phase was analyzed by high performance liquid chromatography (column: Nakalai-Tesque, Cosmocil 5CN-R (4.6 mm×250 mm), eluent: 1 mM phosphoric acid/$H_2O$:acetonitrile=5:1, flow rate 0.7 mL/min., detection: at 210 nm, column temperature: 30° C.) for reaction rate and for the diastereomer ratio of the product tert-butyl(3R,5S)-6-chloro-3,5-dihydroxyhexanoate. The results are shown in Table 1.

TABLE 1

| Strain of microorganism | Reaction rate (%) | Diastereomer ratio (3R, 5S): (3S, 5S) |
|---|---|---|
| Hormoascus platypodis IFO1471 | 39 | 100:0 |
| Candida catenulata IFO0745 | 41 | 100:0 |
| Candida diversa IFO1019 | 33 | 100:0 |
| Candida fructus IFO1581 | 27 | 100:0 |
| Candida glaebosa IFO1353 | 64 | 100:0 |
| Candida guilliermondii IFO0454 | 9 | 100:0 |
| Cryptococcus humicola IFO0760 | 20 | 100:0 |
| Candida intermedia IFO0761 | 24 | 94:6 |
| Candida magnoliae IFO 0705 | 71 | 100:0 |
| Candida musae IFO1582 | 24 | 100:0 |
| Candida pintolopesii var. pintolopesii IFO0729 | 29 | 100:0 |
| Candida pinus IFO0741 | 54 | 100:0 |
| Candida sake IFO0435 | 32 | 100:0 |
| Candida sonorensis IFO10027 | 23 | 100:0 |
| Candida tropicalis IFO1401 | 28 | 95:5 |
| Cryptococcus laurentii IFO0609 | 14 | 100:0 |
| Cryptococcus terreus IFO0727 | 37 | 100:0 |
| Debaryomyces hansenii var. fabryi IFO0058 | 16 | 100:0 |
| Geotrichum eriense ATCC22311 | 24 | 89:11 |
| Kuraishia capsulata IFO0721 | 12 | 100:0 |
| Kluyveromyces marxianus IFO0288 | 8 | 100:0 |
| Pichia bovis IFO1886 | 61 | 95:5 |
| Yamadazyma haplophila IFO0947 | 10 | 100:0 |
| Pichia membranaefaciens IFO0458 | 27 | 95:5 |
| Rhodotorula glutinis IFO1099 | 12 | 100:0 |
| Saccharomyces cerevisiae IFO0718 | 16 | 89:11 |
| Schizoblastsporion kobayasii IFO1644 | 26 | 100:0 |
| Candida claussenii IFO0759 | 24 | 90:10 |
| Debaryomyces robertsii IFO1277 | 20 | 100:0 |
| Zygosaccharmoyces rouxii IFO0493 | 22 | 89:11 |

EXAMPLE 5

Tert-butyl(3R,5S)-6-chloro-3,5-dihydroxyhexanoate

A 5-L mini-jar fermenter containing 3 L of medium A was inoculated with Candida magnoliae IFO0705 and incubated at 30° C. with 0.5 vvm aeration and stirring at 500 rpm for 24 hours. After completion of cultivation, 30 g of tert-butyl (5S)-6-chloro-5-hydroxy-3-oxohexanoate (synthesized by the process described in Example 1) and 60 g of glucose were added and the reaction was carried out, with the pH maintained at 6.5 with sodium hydroxide, for 18 hours. After completion of the reaction, the cells were removed centrifugally and the supernatant was extracted twice using 1.5 L of ethyl acetate each. The organic phase was separated and dehydrated over anhydrous sodium sulfate and the solvent was distilled off by heating under reduced pressure to recover 24 g of tert-butyl(3R,5S)-6-chloro-3,5-dihydroxyhexanoate as a solid. As analyzed by the method described in Example 4, the diastereomer ratio of this product was (3R,5S)/(3S,5S)=100/0. $^1$H-NMR (CDCl$_3$, 400 MHz/ppm): 1.47 (9H, s), 1.62–1.78 (2H, m), 2.43 (2H, d, J=6.4. Hz), 3.51–3.58 (2H, m), 3.75 (1H, bs), 3.84 (1H, bs), 4.07–4.13 (1H, m), 4.23–4.28 (1H, m)

EXAMPLE 6

Tert-butyl 2-[(4R,6S)-6-(chloromethyl)-2,2-dimethyl-1,3-dioxan-4-yl]acetate

In 4.0 mL of acetone was dissolved 1.08 g (4.52 mmol) of tert-butyl(3R,5S)-6-chloro-3,5-dihydroxyhexanoate (synthesized by the process described in Example 5), followed by the addition of 0.83 mL (6.8 mmol) of 2,2-dimethoxypropane and 8.6 mg (0.045 mmol) of p-toluenesulfonic acid in the order mentioned. The mixture was then stirred at room temperature for 4.5 hours, after which the reaction solvent and the excess 2,2-dimethoxypropane were distilled off by heating under reduced pressure. The residue was diluted with 10 mL of saturated sodium hydrogencarbonate/$H_2O$ and extracted 3 times with n-hexane.

The organic extract was washed with saturated aqueous sodium chloride solution and dehydrated over anhydrous sodium sulfate and the solvent was distilled off by heating under reduced pressure to provide 1.25 g (colorless oil) of tert-butyl 2-[(4R,6S)-6-(chloromethyl)-2,2-dimethyl-1,3-dioxan-4-yl]acetate in a yield of 99%.

$^1$H-NMR (CDCl$_3$, 400 MHz/ppm): 1.25 (1H, dd), 1.39 (3H, s), 1.45 (9H, s), 1.47 (3H, s), 1.77 (1H, dt), 2.33 (1H, dd), 2.46 (1H, dd), 2.40 (1H, dd), 2.51 (1H, dd), 4.03–4.10 (1H, m), 4.25–4.30 (1H, m)

EXAMPLE 7

Tert-butyl 2-{(4R,6S)-2,2-dimethyl-6-[(methylcarbonyloxy)methyl]-1,3-dioxan-4-yl}acetate In 10 mL of N,N-dimethylformamide were suspended 1.00 g (3.60 mmol) of tert-butyl 2-[(4R,6S)-6-(chloromethyl)-2,2-dimethyl-1,3-dioxan-4-yl]acetate (synthesized by the process described in Example 6), 1.16 g (3.60 mmol) of tetra-n-butylammonium bromide and 1.76 g (18.0 mmol) of potassium acetate, and the suspension was stirred at 100° C. for 20 hours. After cooling to room temperature, the reaction mixture was diluted with 20 mL of water and extracted 3 times using n-hexane.

The organic extract was washed with saturated aqueous sodium chloride solution and dehydrated over anhydrous sodium sulfate and the solvent was distilled off by heating under reduced pressure. The residue was purified by silica-gel column chromatography (Merck's Kieselgel 60, hexane-:ethyl acetate=80:20) to provide 0.88 g of tert-butyl 2-{(4R, 6S)-2,2-dimethyl-6-[(methylcarbonyloxy)methyl]-1,3-dioxan-4-yl}acetate (white solid) in a yield of 81%.

$^1$H-NMR (CDCl$_3$, 400 MHz/ppm): 1.27 (1H, dd, J=23.9, 11.7 Hz), 1.39 (3H, s), 1.45 (9H, s), 1.47 (3H, s), 1.57 (1H, dm, J=10.3 Hz), 2.08 (3H, s), 2.32 (1H, dd, J=15.1, 5.9 Hz), 2.45 (1H, dd, J=15.1, 6.8 Hz), 3.97–4.16 (3H, m), 4.25–4.33 (1H, m)

EXAMPLE 8

Tert-butyl 2-{(4R,6S)-2,2-dimethyl-6-[(methylcarbonyloxy)methyl]-1,3-dioxan-4-yl}acetate In 10 mL of N,N-dimethylformamide were suspended 1.00 g (3.60 mmol) of tert-butyl 2-[(4R,6S)-6-(chloromethyl)-2,2-dimethyl-1,3-dioxan-4-yl]acetate [synthesized by the process described in Example 6], 0.5 g (1.80 mmol) of tetra-n-butylammonium chloride and 0.89 g (10.8 mmol) of sodium acetate, and the suspension was stirred at 100° C. for 20 hours. After cooling to room temperature, the reaction mixture was diluted with 20 mL of water and extracted 3 times with n-hexane.

The organic extract was washed with saturated aqueous sodium chloride solution and dehydrated over anhydrous sodium sulfate and the solvent was distilled off by heating under reduced pressure. To the residue was added 8.0 mL of n-hexane again, and the mixture was heated at 50° C. for dissolution, followed by cooing to −20° C. The crystals which separated out were recovered by filtration, washed with cold n-hexane and dried by heating under reduced pressure to provide 0.76 g of tert-butyl 2-{(4R,6S)-2,2-dimethyl-6-[(methylcarbonyloxy)methyl]-1,3-dioxan-4-yl}acetate (white needles) in a yield of 70%.

EXAMPLE 9

Tert-butyl 2-[(4R,6S)-6-(hydroxymethyl)-2,2-dimethyl-1,3-dioxan-4-yl]acetate

In 100 mL of methanol was dissolved 10 g (33.1 mmol) of tert-butyl 2-{(4R,6S)-2,2-dimethyl-6-[(methylcarbonyloxy)methyl]-1,3-dioxan-4-yl}acetate [synthesized by the process described in Example 8], and under ice-cooling and stirring, 0.46 g (3.3 mmol) of potassium carbonate was added. The mixture was further stirred under ice-cooling for 4 hours. From this reaction mixture, the reaction solvent was distilled off by heating under reduced pressure, and the residue was diluted with 50 mL of water and neutralized with 0.1 N-hydrochloric acid. This solution was extracted with ethyl acetate and the resulting organic layer was washed with water and dehydrated over anhydrous sodium sulfate. The solvent was then distilled off by heating under reduced pressure. The oily residue was decompressed to 1 Torr or less with a vacuum pump to remove the solvent almost thoroughly. As a result, 8.6 g of tert-butyl 2-[(4R,6S)-6-(hydroxymethyl)-2,2-dimethyl-1,3-dioxan-4-yl]acetate (colorless oil) was obtained in a yield of 100%.

$^1$H-NMR (CDCl$_3$, 400 MHz/ppm): 1.29–1.52 (2H, m), 1.39 (3H, s), 1.45 (9H, s), 1.47 (3H, s), 2.05 (1H, bs), 2.33 (1H, dd, J=15.1, 5.9 Hz), 2.44 (1H, dd, J=15.1, 6.8 Hz), 3.47–3.53 (1H, m), 3.58–3.64 (1H, m), 3.99–4.04 (1H, m), 4.27–4.33 (1H, m)

EXAMPLE 10

Tert-butyl(3R,5S)-6-chloro-3,5-dihydroxyhexanoate

Large-sized test tubes were charged with 7 mL of said medium B and, after sterilization, inoculated with the bacteria shown in Table 2, respectively. Then, aerobic shake culture was carried out at 30° C. for 1 day. From the resulting culture broth, the cells were harvested by centrifugation and suspended in 0.5 mL of 50 mM phosphate buffer (pH 6.5) containing 0.5% of tert-butyl(5S)-6-chloro-5-hydroxy-3-oxohexanoate and 1.5% of glucose. The suspension was placed in a 10 mL test tube equipped with a stopper and the reaction was carried out under shaking at 30° C. for 20 hours. After completion of the reaction, the reaction mixture was extracted with 0.5 mL of ethyl acetate and the ethyl acetate phase was analyzed by high performance liquid chromatography (column: Nakalai-Tesque's Cosmocil 5CN-R (4.6 mm×250 mm), eluent: 1 mM phosphoric acid/H$_2$O:acetonitrile=5:1, flow rate: 0.7 mL/min., detection: at 210 nm, column temperature: 30° C.) for reaction rate and for the diastereomer ratio of the product tert-butyl(3R,5S)-6-chloro-3,5-dihydroxyhexanoate. The results are shown in Table 2.

TABLE 2

| Strain of microorganism | Reaction ratio % | Diastereomer (3R, 5S): (3S, 5S) |
|---|---|---|
| Brevibacterium stationis IFO12144 | 37.1 | 94:6 |
| Corynebacterium ammoniagenes IFO12072 | 29.2 | 92:8 |
| Corynebacterium flavescens IFO14136 | 37.7 | 94:6 |
| Corynebacterium glutamicum ATCC13287 | 19.6 | 94:6 |
| Rhodococcus erythropolis IAM1474 | 24.8 | 82:17 |

EXAMPLE 11

Tert-butyl(5S)-6-chloro-5-hydroxy-3-oxohexanoate

Under argon gas, a solution composed of 2.67 g (26.4 mmol) of diisopropylamine and 5 ml of tetrahydrofuran was added dropwise to 15 mL (240 mmol) of a solution of n-butyllithium (1.5 mol/L) in hexane at 5° C. with constant stirring to prepare a lithium diisopropylamide solution.

Separately, 240 mg (6 mmol equivalent) of sodium hydride (60% in mineral oil) was washed with hexane and, then, 6 ml of tetrahydrofuran was added. Then, at 5° C., 1.71 g (18.0 mmol) of magnesium chloride, 1.74 g (15.0 mmol) of tert-butyl acetate and 1.0 g (6 mmol) of ethyl(3S)-4-chloro-3-hydroxybutyrate were added and the mixture was stirred for 30 minutes. To this mixture, the lithium diisopropylamide solution prepared above was added dropwise over 10 minutes at the same temperature and the reaction mixture was further stirred at an elevated temperature of 25° C. for 3 hours.

The above reaction mixture was poured in a mixture of 6.47 g of concentrated sulfuric acid and 10 ml of water. After the aqueous layer was separated, the organic layer was washed with 10 ml of water and the solvent was distilled off by heating under reduced pressure to provide 1.78 g of oil. Analysis of this product by the method described in Example 2 revealed that the yield was 64%.

Comparative Example 2

Tert-butyl(5S)-6-chloro-5-hydroxy-3-oxohexanoate

Omitting the addition of magnesium chloride, the procedure of Example 11 was otherwise repeated. As analyzed by the method described in Example 2, the yield was 3%.

INDUSTRIAL APPLICABILITY

In accordance with the present invention described above, an optically active 2-[6-(hydroxymethyl)-1,3-dioxan-4-yl]

acetic acid derivative of value as a pharmaceutical intermediate, particularly the intermediate of an HMG-CoA reductase inhibitor, can be produced from an inexpensive, readily available starting material without requiring any special equipment such as low-temperature reaction equipment.

What is claimed is:

1. A process for producing a compound of the following general formula (I):

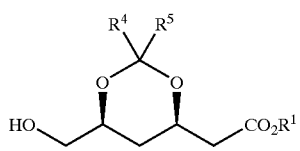
(I)

wherein $R^1$ represents hydrogen, an alkyl group of 1 to 12 carbon atoms, an aryl group of 6 to 12 carbon atoms or an aralkyl group of 7 to 12 carbon atoms, $R^4$ and $R^5$ each independently represents hydrogen, an alkyl group of 1 to 12 carbon atoms, an aryl group of 6 to 12 carbon atoms or an aralkyl group of 7 to 12 carbon atoms, and $R^4$ and $R^5$ may be bound to each other to form a ring, which comprises (1) reacting an enolate prepared by permitting either a base or a metal having a valency of 0 to act on an acetic ester derivative of the following general formula (II)

(II)

wherein $R^1$ represents hydrogen, an alkyl group of 1 to 12 carbon atoms, an aryl group of 6 to 12 carbon atoms an aralkyl group of 7 to 12 carbon atoms, and $X^2$ represents hydrogen or a halogen atom, with a compound of the following general formula (III):

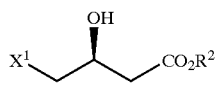
(III)

wherein $R^2$ represents an alkyl group of 1 to 12 carbon atoms, an aryl group of 6 to 12 carbon atoms or an aralkyl group of 7 to 12 carbon atoms, and $X^2$ represents a halogen atom, at a temperature of not less than −30° C. to give a compound of the following general formula (IV):

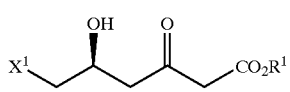
(IV)

wherein $R^1$ and $X^1$ are as defined above, (2) reducing this compound with the aid of a strain of microorganism to give a compound of the following general formula (V):

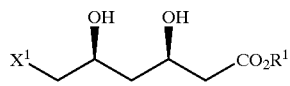
(V)

wherein $R^1$ and $X^1$ are as defined above, (3) treating this compound with an acetalizing agent in the presence of an acid catalyst to give a compound of the following general formula (VI):

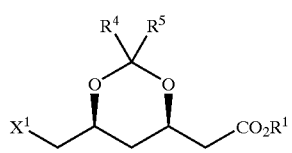
(VI)

wherein $R^1$ and $X^1$ are as defined above, $R^4$ and $R^5$ each independently represents hydrogen, an alkyl group of 1 to 12 carbon atoms, an aryl group of 6 to 12 carbon atoms or an aralkyl group of 7 to 12 carbon atoms, and $R^4$ and $R^5$ may be bound to each other to form a ring, (4) acyloxylating this compound with an acyloxylating agent to give a compound of the following general formula (VII):

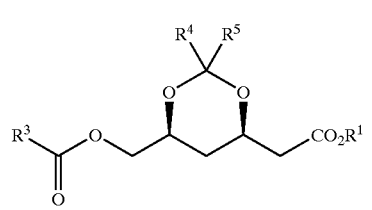
(VII)

wherein $R^1$, $R^4$ and $R^5$ are as defined above, $R^3$ represents hydrogen, an alkyl group of 1 to 12 carbon atoms, an aryl group of 6 to 12 carbon atoms or an aralkyl group of 7 to 12 carbon atoms, and (5) subjecting this compound to solvolysis in the presence of a base, wherein the strain of microorganism used in the step (2) is selected from the group of genera of microorganisms consisting of Hormoascus, Candida, Cryptococcus, Debaryomyces, Geotrichum, Kuraishia, Hansenulla, Kluyveromyces, Pichia, Yamadazyma, Rhodotorula, Saccharomyces, Schizoblastosporon, Zygosaccharomyces, Brevibacterium, Corynebacterium, and Rhodococcus.

2. The process according to claim 1 wherein $X^2$ in the acetic ester derivative is a hydrogen atom and the base used for preparation of the enolate is a magnesium amide of the following general formula (VIII):

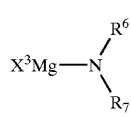
(VIII)

wherein $R^6$ and $R^7$ each represents an alkyl group of 1 to 12 carbon atoms, an aryl group of 6 to 12 carbon atoms, an aralkyl group of 7 to 12 carbon atoms, or a silyl group, and $X^3$ represents a halogen atom.

3. The process according to claim 2 wherein, in the magnesium amide, $R^6$ and $R^7$ are isopropyl groups.

4. The process according to claim 2 wherein, in the magnesium amide, $X^3$ is a chlorine atom.

5. The process according to claim 1 wherein $X^2$ in the acetic ester derivative is a halogen atom and magnesium or zinc is used as the metal having a valency of 0 for preparation of the enolate.

6. The process according to claim 1 wherein a polyether is added at the reaction of the enolate.

7. The process according to claim 6 wherein dimethoxyethane is used as the polyether.

8. The process according to claim 1 which, in the step of the reduction reaction with the aid of a strain of microorganism, uses a culture broth of the strain of microorganism, a cellular fraction thereof or a processed matter thereof.

9. The process according to claim 1 which, in the step of the reduction reaction with the aid of a strain of microorganism, uses a strain of microorganism selected from among the genera and species of microorganisms belonging to: *Hormoascus platypodis, Candida catenulata, Candida diversa, Candida fructus, Candida glaebosa, Candida guilliermondii, Cryptococcus humicola, Candida intermedia, Candida magnoliae, Candida musae, Candida pintolopesii* var. *pintolopenii, Candida pinus, Candida sake, Candida sonorensis, Candida tropicalis, Cryptococcus laurentii, Cryptococcus terreus, Debaryomyces hanseii* var. *fabryi, Geotrichum eriense, Kuraishia capsulata, Kluyveromyces marxianus, Pichia bovis, Yamadazyma haplophila, Pichia membranaefaciens, Rhodotorula glutinis, Saccharomyces cerevisiae, Schizoblastosporon kobayasii, Candida claussenii, Debaryomyces robertsii, Zygosaccharomyces rouxii, Brevibacterium stationis, Corynebacterium ammoniagenes, Corynebacterium flavescens, Corynebacterium glutamicum,* and *Rhodococcus erythropolis.*

10. The process according to claim 1 wherein a carboxylic acid quaternary ammonium salt of the following general formula (XI) is used as the acyloxylating agent:

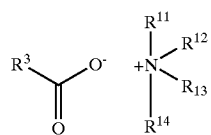

(XI)

wherein $R^3$ represents hydrogen, an alkyl group of 1 to 12 carbon atoms, an aryl group of 6 to 12 carbon atoms or an aralkyl group of 7 to 12 carbon atoms, $R^{11}$, $R^{12}$, $R^{13}$ and $R^{14}$ each independently represents an alkyl group of 1 to 12 carbon atoms, an aryl group of 6 to 12 carbon atoms or an aralkyl group of 7 to 12 carbon atoms.

11. The process according to claim 10 wherein, in the carboxylic acid quaternary ammonium salt, all of $R^{11}$, $R^{12}$, $R^{13}$ and $R^{14}$ are n-butyl groups.

12. The process according to claim 1 wherein the acyloxylating agent is a mixture of a quaternary ammonium salt of the following general formula (XII):

(XII)

wherein $R^{15}$, $R^{16}$, $R^{17}$ and $R^{18}$ each independently represents an alkyl group of 1 to 12 carbon atoms, an aryl group of 6 to 12 carbon atoms or an aralkyl group of 7 to 12 carbon atoms, and $X^5$ represents a halogen atom, a hydroxyl group or an acyloxy group, and a carboxylic acid salt of the following general formula (XIII):

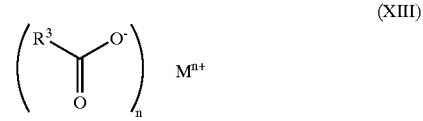

(XIII)

wherein $R^3$ represents hydrogen, an alkyl group of 1 to 12 carbon atoms, an aryl group of 6 to 12 carbon atoms or an aralkyl group of 7 to 12 carbon atoms, M represents an alkali metal or an alkaline earth metal, and n represents an integer of 1 or 2.

13. The process according to claim 12 wherein, in the quaternary ammonium salt, all of $R^{15}$, $R^{16}$, $R^{17}$ and $R^{18}$ are n-butyl groups.

14. The process according to claim 12 wherein, in the quaternary ammonium salt, $X^5$ is either chlorine or bromine.

15. The process according to claim 12 wherein, in the carboxylic acid salt, M is either sodium or potassium.

16. The process according to claim 12 wherein the quaternary ammonium salt is used as a catalyst in an amount of not more than the stoichiometric amount.

17. The process according to claim 1 wherein N,N-dimethylformamide is used as a solvent for acyloxylation reaction.

18. The process according to claim 1 wherein $R^1$ is a tert-butyl group.

19. The process according to claim 1 wherein $R^2$ is an ethyl group.

20. The process according to claim 1 wherein $R^3$ is a methyl group.

21. The process according to claim 1 wherein both of $R^4$ and $R^5$ are methyl groups.

22. The process according to claim 1 wherein $X^1$ is chlorine.

* * * * *

UNITED STATES PATENT AND TRADEMARK OFFICE
CERTIFICATE OF CORRECTION

PATENT NO. : 6,472,544 B1
DATED : October 29, 2002
INVENTOR(S) : Kizaki et al.

It is certified that error appears in the above-identified patent and that said Letters Patent is hereby corrected as shown below:

<u>Title page, Item [54] and Column 1, lines 1-4,</u>
Title, change "PROCESS FOR THE PREPARATION OF OPTICALLY ACTIVE 2-[6-HYDROXYMETHYL)-1, 3-DIOXAN-4YL) ACETIC ACID DERIVATIVES", to -- PROCESS FOR THE PREPARATION OF OPTICALLY ACTIVE 2-[6-(HYDROXYMETHYL)-1, 3-DIOXAN-4-YL] ACETIC ACID DERIVATIVES --

<u>Column 23,</u>
Line 40, change "an aralkyl group of 7 to 12 carbon atoms, and $X^2$" to -- or an aralkyl group of 7 to 12 carbon atoms, and $X^2$ --
Line 52, change "aralkyl group of 7 to 12 carbon atoms, and $X^2$ repre-" to -- aralkyl group of 7 to 12 carbon atoms, and $X^1$ repre- --

<u>Column 24,</u>
Line 60, Formula (VIII) change

" 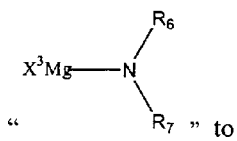 " to

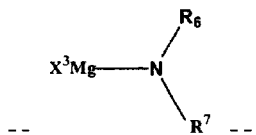 --

UNITED STATES PATENT AND TRADEMARK OFFICE
CERTIFICATE OF CORRECTION

PATENT NO. : 6,472,544 B1
DATED : October 29, 2002
INVENTOR(S) : Kizaki et al.

It is certified that error appears in the above-identified patent and that said Letters Patent is hereby corrected as shown below:

Column 26,
Lines 5-10, Formula (XII) change

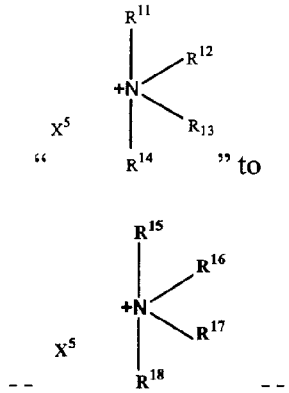 to

Signed and Sealed this

Twenty-fourth Day of June, 2003

JAMES E. ROGAN
*Director of the United States Patent and Trademark Office*